United States Patent [19]
Joseph

[11] Patent Number: 5,939,071
[45] Date of Patent: Aug. 17, 1999

[54] PROCESS FOR PRODUCING PHARMACEUTICAL PREPARATIONS HAVING A HIGHER CONTENT OF ACTIVE PLANT INGREDIENTS

[76] Inventor: Heinz Walter Joseph, Marie Juchacz-Weg 17, D-71522 Backnang, Germany

[21] Appl. No.: 08/918,528

[22] Filed: Aug. 21, 1997

[51] Int. Cl.⁶ .......................... A01N 65/00; A01N 25/12; F26B 11/12; F26B 3/24

[52] U.S. Cl. .................................. 424/195.1; 424/195.1; 514/783; 34/291; 34/406

[58] Field of Search .................. 424/195.1; 514/783; 24/98, 23; 34/408, 426, 291, 406

[56] References Cited

U.S. PATENT DOCUMENTS

| | | | |
|---|---|---|---|
| 4,469,685 | 9/1984 | Kojima et al. | 424/195 |
| 4,506,838 | 3/1985 | Riniker et al. | 241/98 |
| 4,674,692 | 6/1987 | Killer et al. | 241/98 |
| 5,053,222 | 10/1991 | Takasu et al. | 424/7 |
| 5,466,455 | 11/1995 | Huffstutler et al. | 424/401 |
| 5,494,668 | 2/1996 | Patwarden | 424/195.1 |
| 5,616,356 | 4/1997 | Buhler et al. | 426/443 |

FOREIGN PATENT DOCUMENTS

| | | |
|---|---|---|
| 0753306A1 | 1/1997 | European Pat. Off. . |
| WO 95/03380 | 2/1995 | WIPO . |

OTHER PUBLICATIONS

L. Panizzi, "Composition and antimicrobial properties of essential oils of four Mediterranean Lamiaceae" Journal of Ethmopharmacology 39, pp. 167–170, (1993) no month given.

parG. Vampa, "Études Chimiques Et Microbiologiques Sur Les Huiles Essentielles De Thymus", Plantes Mediciuales et Plhytotherapie 22 (3), pp. 195–202, (1988) no month given.

D. Göckeritz et al., "Terpene und Terpenderivate vom Carvon–und Camphertyp–ihre antimikrobiellen und verminoxen Eigenschaften", Sektion Pharmazie und Hygiene–Institut, Pharmize 29, H.5 (1974), pp. 339–344 no month given.

Pilot Vacuum Dryer, INOX Glatt AG Switzerland no date given.

Vacuum Dryers, INOX Glatt AG Switzerland no date given.

*Primary Examiner*—Kathleen K. Fonda
*Assistant Examiner*—Marjorie A. Moran

[57] ABSTRACT

The present invention relates to a process for preparing dry plant extracts and pharmaceutical preparations containing such extracts having a high content of active plant ingredients such as essential oils and phenols wherein a fluid extract or a tincture of drugs is typically fed into the drying system Inox Maurer or Inox Glatt®, e.g. IUT 20, IUT 50, IUT 100 or IUT 2000, and dried at a starting and return temperature between 120 and 5° C., a preferred interior temperature between 10 and 80° C., especially preferably between 25 and 70° C., and a pressure between 0.5 and 1000 mbar, preferably between 5 and 100 mbar and especially preferably between 30 and 70 mbar, said drying being effected while the stirrer runs between 0 and 10 rpm, preferably between 2 and 5 rpm, and at a rotational speed of the chopper between 200 and 800 rpm. The process according to the invention results in pharmaceutical preparations having a markedly increased level of active plant ingredients and, simultaneously, offering economic and ecological advantages.

21 Claims, 1 Drawing Sheet

PROCESS FOR PRODUCING PHARMACEUTICAL PREPARATIONS HAVING A HIGHER CONTENT OF ACTIVE PLANT INGREDIENTS

The present invention relates to processes for producing dry plant extracts and to pharmaceutical compositions having a high share of active plant ingredients such as essential oils and phenols containing the same. Essential oils and phenols as found in plants are known to have anti-inflammatory, bacteriostatic, hyperaemisating and secretolytic effects (cf., for example, *Pharmazie* 29 (5) 339, 1974; *Journal of Ethnopharmacology* 39, 167–170, 1993; *Plantes Medicinales et Phytotherapie*, 22 (3), 195–202, 1988). In many cases, these effects are linearly dependent on the dosage.

DAB 10 (Deutsches Arzneibuch, $10^{th}$ edition) defines minimum contents of these essential oils and phenols for the quality of a drug so as to ensure a safe therapy.

The requirements of DAB 10 are exemplified on *Herba thymi* (thyme), parent plant *Thymus vulgaris* L. According to DAB 10, *Herba thymi* (the drug used) must contain at least 1.2% of essential oil and at least 0.5% of phenol which is calculated as thymol.

The uniformity of the extracts and the high content of essential oils is a significant criterion for finished preparations. Owing to their physical properties, essential oils are substances which are highly volatile and oxidise easily. Phenols also oxidise readily.

For this reason, there is a high risk that these substances decompose during production of preparations and that the effectiveness of the pharmaceutical preparation is affected by the oxidisability of the compounds which contain many double bonds.

In addition to classical distillation and drying under regular conditions, the accepted drying processes hitherto employed in the pharmaceutical industry also comprise processes which utilise the variation of pressure and temperature in order to obtain dry extracts.

The classical process for producing dry extracts is to prepare a fluid extract or a tincture. After the solvents are distilled off, a spissum extract (viscous extract) is obtained to which excipients and/or additives such as lactose, polyvinyl pyrrolidone, sucrose, silica etc. are often added. This humid, viscous mass is then processed into the desired dry extract preparation in rack chambers or dryers. Due to distillation under regular conditions, the high temperatures required for the final drying and the lack of oxygen occlusion, it is known that many by-products are found which occur as a result of this production process and may have a deterimental effect.

A process which is frequently used in the preparation of dry extracts is the so-called vacuum band drying process. In this process, the spissum extract is processed to a dry extract preparation after a pre-drying stage by means of a downflow evaporator. The temperatures, pressures and material throughput parameters used in this process provide extracts having a low content of essential oils and phenols. In this process, the temperatures are between 50 and 105° C. and the pressure at approx. 18 mbar. These processes also cause losses of active plant ingredients and especially phenolic and essential oil substances. Among other things, this is due to a lack of movement of the product to be dried (e.g. diffusion effects).

The drying process by means of a turbulent-layer dryer requires temperatures between approx. 47 and 117° C. Despite blowing in nitrogen (and reducing the oxygen content), a residue of about 5% oxygen is still found which initiates a number of detrimental processes. Drying in this process is carried out under normal pressure conditions. This explains the low contents especially of phenolic substances and essential oils. In this process, it is also possible to vary the parameter temperature which does not result in an increased yield in essential oils.

It is therefore the objective of the present invention to provide processes for preparing dry plant extracts which are made of plants containing active ingredients, especially essential oils and phenols, which largely avoid the disadvantages outlined above.

The production process according to the invention which uses a commercial Inox Glatt®, formerly Inox Maurer, vacuum dryer illustrated in greater detail below surprisingly shows that the parameters of pressure and temperature have different effects in this system than, for example, in the sector of vacuum band drying.

The process according to the invention for producing plant extracts and pharmaceutical preparations containing the same with a high content of active plant ingredients comprises the steps of feeding a fluid extract obtained in the customary and known manner or a tincture of drugs into a vacuum drying system equipped with a chopper and a stirrer, e.g. the dryers of Inox Maurer or Inox Glatt®, respectively. Among these commercial appliances, it is possible to use the types designated IUT 20, IUT 50, IUT 100 and IUT 2000 as well as other types from the IUT series depending on the batch size required.

The vacuum drying system comprises the following features: a multi-blade stirrer extending through the cylindrical mixing and drying chamber and having its own drive and, if required, comprising a vapour filter, a back-purge device, a condenser for the solvent comprising an aftercooler and a collecting vessel, a retrograde condenser and a process, control and regulation unit as well as, optionally, pelletising dies. Its special features are a chopper extending throughout the entire depth of the drying and mixing chamber having a drive which is independent of the stirrer and a comb-shaped stator for increasing the chopper effect through which the chopper knives rotate.

At the beginning of the drying process, a starting and return temperature between 120 and 5° C. is adjusted and the drying process conducted at an interior temperature between 10 and 80° C., preferably between 25 and 70° C., and a vapour temperature between 15° C. to 55° C. The pressure varies between 0.5 and 1000 mbar, preferably between 5 and 100 mbar and especially preferably between 30 and 70 mbar. The drying process must be carried out while the stirrer runs between 0 and 10 rpm, preferably between 2 and 5 rpm. The chopper operates at a rotational speed of up to 1200 rpm, preferably between 200 and 800 rpm. The preferred vapour temperature is 18 to 38° C., or 20 to 40° C. respectively. Depending on the product and the parameters used in individual cases, the drying time and the measurements concerning drying losses (Trocknungsverlust=TV) are determined regularly (see table 1). In general, the drying process is completed with a drying loss between 0 and 10% and at a drying time between 4 and 24 hours.

Using the preparation of thyme dry extract as an example, it was possible to show that a far greater content of essential oils and phenols was found when comparing the process according to the invention with common processes of the prior art. The extract of *Cimicifuga rhiz.* recovered according to the invention surprisingly also showed similar increased contents of active ingredients, the active ingredient in question being a triterpenoid (cf. example 2).

This finding was highly surprising as shown by the comparative experiment described below.

Treating the liquid extracts in accordance with the invention ensures the most gentle preparation of dry extracts from drugs containing active ingredients, especially essential oils. All other drying processes result in much higher losses and thus a reduction of the potential therapeutic success. This is also of significant advantage in the important standardisation of the content of the active ingredient.

In addition, the process according to the invention in connection with the special apparatus provides the possibility to gently recover and reuse solvents used for the preparation of fluid extracts. Not even very small amounts are vented into the atmosphere since pertinent condenser means at the dryer itself permit recovery of the solvents. This also takes into account strict environmental regulations without requiring complicated additional or down-stream technical steps or devices.

Another advantage lies in the fact that the physical consistency of the product is increased and that even dry extracts going through viscous, sticky, pasty or lump-forming intermediate stages may be produced.

It is another unexpected advantage that the process according to the invention permits continuous processing of the dry extract just obtained into finished or semi-finished pharmaceutical preparations by subsequent mixing with one or several additional dry extracts or other extracts and/or active ingredients and/or pelletising and/or dilution in the same drying system without the extract having to be removed.

The product in powder form obtained after completion of the drying process may be processed into the desired drug and administration forms by methods generally known in pharmaceutical technology and galenics.

The process according to the invention was carried out by drying additional starting materials as described above and comparable results were obtained. These drugs were Echinacea, *Agnus castus*, *Allium cepa* (onion), Hipposcastanus (horse chestnuts), *Hedera helix* (ivy), Curcuma (turmeric) and *Galphimia glauca*.

In addition, liquid mixed extracts jointly produced from various dried drugs were dried by means of the process according to the invention.

The following examples are intended to illustrate the invention without limiting it.

EXAMPLE 1

In order to prepare the various tinctures used, different batches of *Herba thymi* were employed. The tincture obtained from the drug was prepared by means of 70% (v/v) ethanol and the phenol content determined.

The content of essential oils was only determined in the starting drug, since it is difficult to analyse it from the tincture form.

After the optional addition of the customary additives (17% of glucose syrup and 3% of silica), part of the tincture was dried by conventional processes (vacuum band drying and turbulent-layer drying) whereas the remaining part was dried by the process of the invention.

Several experiments were carried out for the process according to the invention. The amount of tincture used varied between 50 and 2000 liters. The tincture was sucked into Inox/Glatt or Maurer vacuum dryers, respectively (IUT 20, IUT 50, IUT 100, IUT 2000), at room temperature and dried between 120° C. and 5° C. starting and return temperature.

The temperature in the reaction chamber during production was between 25 and 70° C. and the pressure between 30 and 70 mbar (FIG. 1).

Figure 1:
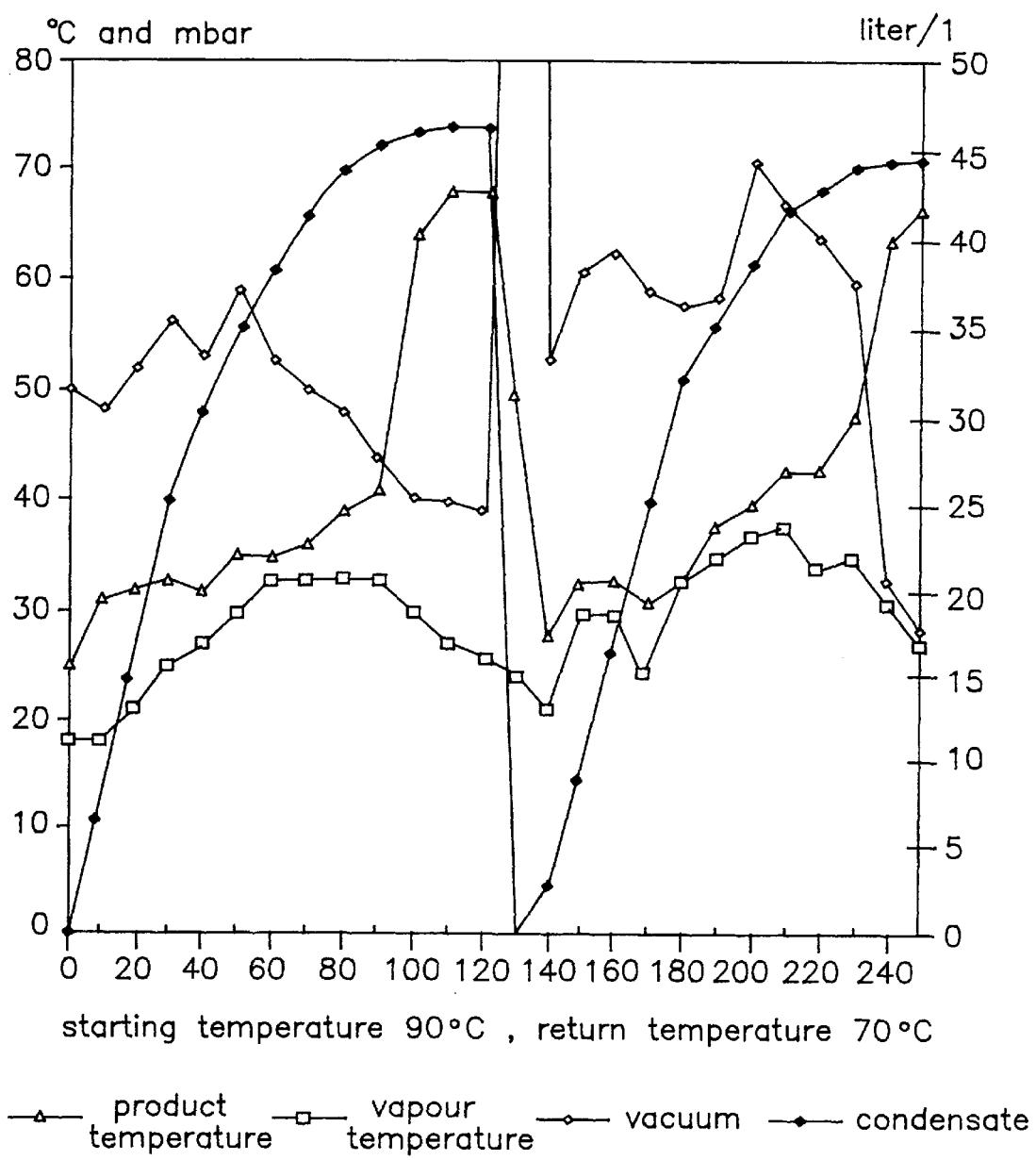
FIG. 1 shows the course of the product temperature, the filter temperature (vapour temperature), the pressures and the amount of condensate measured when drying the thyme fluid extract according to the example in an IUT 100 apparatus.

The evaporation output was between 300 and 330 l/h; however it is subject to variations due to the amount of alcohol which is distilled off easily at the beginning in comparison with the less volatile water. After the desired drying loss was reached, the dried material was removed and the drying loss (see table 1), the phenols content (see table 2) and the essential oils content (see table 3) were determined. As pointed out above, the percentages concerning the ratio of rediscovery of essential oils in tables 2 and 3 refer to the starting drug and the percentages for phenols to the starting tincture.

TABLE 1

Drying losses or drying residue, respectively

|  | Drying loss or drying residue |
|---|---|
| Thyme tincture | 2.11% |
| Dry extract Inox-Maurer/Glatt native (without additives) | 5.81% |
| Dry extract Inox-Maurer/Glatt with additives (glucose syrup, silica) | 4.35% |
| Dry extract turbulent-layer drying, native (prior art/comparison) | 6.21% |
| Dry extract vacuum belt drying (prior art/comparison) | 2.92% |

TABLE 2

Phenol content

|  | Phenol content calculated as thymol | Rediscovery rate |
|---|---|---|
| Thyme tincture | 0.0935% | — |
| Dry extract Inox-Maurer/Glatt native (without additives) | 1.632% | 37% |
| Dry extract Inox-Maurer/Glatt with additives (glucose syrup, silica) | 1.262% | 35% |
| Dry extract turbulent-layer drying, native (prior art/comparison) | 0.609% | 12% |
| Dry extract vacuum belt drying (prior art/comparison) | 0.164% | 4.5% |

TABLE 3

Contents of essential oils

|  | Content of essential oils | Rediscovery rate |
|---|---|---|
| Thyme drug | 2.25% | — |
| Dry extract Inox-Maurer/Glatt native (without additives) | 3.08% | 29% |
| Dry extract Inox-Maurer/Glatt with additives (glucose syrup, silica) | 1.95% | 22% |

TABLE 3-continued

Contents of essential oils

| | Content of essential oils | Rediscovery rate |
|---|---|---|
| Dry extract turbulent-layer drying, native (prior art/comparison) | 1.25% | 12% |
| Dry extract vacuum belt drying (prior art/comparison) | 0.35% | 4.0% |

As the above tables 2 and 3 show, the process of the invention provides a far higher content of essential oils and phenols in comparison to the known processes.

The drying process is completed within approx. 4 hours when 84 kg of tincture are used. Care must be taken that the stirrer and chopper of the apparatus stay in motion to prevent the feed material from getting viscous or lumpy so that the feared clotting of the dryer does not occur.

EXAMPLE 2

Cycloartenolic triterpenoids are mentioned as examples of other plant ingredients. These substances are especially contained in Cimicifuga. 27-deoxyacteine may be mentioned as an exemplary representative contained in Cimicifuga.

The extracts are customarily prepared by a circulation process at an elevated temperature (approx. 50° C., ratio 1:1) and subsequent drying in rack chambers at 105° C.

The starting material is the dried and cut active drug which is present in a loose sack. It is extracted at an temperature and thickened to a spissum extract. Then lactose is added as an excipient.

In addition to an exact adjustment of the drug-extract ratio the process of the invention provides significantly higher 27-deoxyacteine yields. The drying process was conducted under a reduced pressure of <300 mbar and at a maximum drying temperature of 50 to 60° C. in the reaction chamber. The evaporation output was 15 l/h. The drying of 100 kg of tincture was complete 35 hours.

The extract dried by means of an Inox/Glatt® apparatus has a band width of (3.9–4.3%) 27-deoxyacteine content whereas the extracts dried by the conventional process (see table 1) had contents of 1.7–2.0%.

TABLE 4

| New process 27-deoxyacteine % | | Prior art 27-deoxyacteine % | |
|---|---|---|---|
| Batch | Content | Batch | Content |
| 96120416 | 3.95 | 5933 | 1.71 |
| 96120917 | 3.85 | 5937 | 1.98 |
| 96121018 | 4.26 | 5938 | 1.90 |

EXAMPLE 3

The following examples list formulations for medicaments based on the extracts obtained by the process of the invention:

A) Cimicifuga preparation

Active drug ingredients: 1.66–2.86 mg of dry extract of a Cimicifuga rootstock which corresponds to 20 mg of drug Other ingredients: lactose×1H$_2$O (as standardising agent), ammonium methacrylate copolymer, microcrystalline cellulose, iron oxide hydrate (E 172), ferric oxide (E 172), potato starch, Macrogol 6000, magnesium stearate, Polyvidon 30 (Poly(1-vinyl-2-pyrrolidone)), talcum, titanium dioxide (E 171), highly dispersed silica.

Final weight: 125.0 mg

B) *Agnus castus* preparation

Active drug ingredients: Dry extract of *Agnus castus* 3.2–4.8 mg

Other ingredients: Polyvidon 30, highly dispersed silica, potato starch, lactose×1H$_2$O, microcrystalline cellulose, magnesium stearate, talcum, titanium dioxide (E 171), iron oxide hydrate (E 172), indigotin varnish (E 132), macrogol 6000 (poly(ethyl acrylate methyl methacrylate trimethyl ammonium ethylacrylate chloride)) 1:2:0.2, molecular weight 150.000)

Final weight: 125.0 mg

I claim:

1. A process for preparing dry plant extracts by feeding plant material to be dried into a vacuum drying system consisting of a chopper and a stirrer, the chopper and the stirrer adapted to be rotated at different speeds, and drying the plant material in the vacuum drying system under conditions where a starting and return temperature is between 120 and 5° C., an interior temperature is between 10 and 80° C., a vapor temperature of between 15° C. to 55° C. and a pressure between 0.5 and 1000 mbar, said drying being effected while the stirrer is rotated between 0 and 10 rpm, and the chopper is rotated between 200 and 800 rpm.

2. A process according to claim 1, wherein the material is dried at an interior temperature between 25 and 75° C.

3. A process according to claim 2 wherein the material is dried at a pressure between 30 and 70 mbar.

4. A process according to claim 2 wherein the material is dried while the stirrer runs at 2 to 5 rpm.

5. A process according to claim 1, wherein the material is dried at a pressure between 5 and 100 mbar.

6. A process according to claim 1, wherein the material is dried while the stirrer runs at 2 to 5 rpm.

7. A process according to claim 1, wherein said vacuum drying comprising a multi-blade stirrer extending through a cylindrical mixing and drying chamber, the vacuum drying system further comprising a vapor filter, a back-purge device, a solvent condenser comprising an after-cooler and a collecting vessel, a retrograde condenser and a process control and regulation unit, the vacuum drying system equipped with a chopper extending throughout the entire depth of the drying and mixing chamber, the chopper having knives rotating through a comb-shaped stator.

8. A process according to claim 7 further including pelletizing dies.

9. A process according to claim 1, wherein a dry extract thus obtained is processed continuously without removal or interim storage into finished pharmaceutical preparations by subsequent steps, being one of or mixtures of, mixing with one or several other dry extracts, other extracts, active ingredients, pelletizing or diluting the dry extract.

10. A process according to claim 1, wherein the plant used is one of Echinacea, *Agnus castus, Allium cepa, Hedera helix*, Hippocastanus, Curcuma, *Galphimia glauca* or *Herba thymi*.

11. A process according to claim 1, wherein a mixed extract is prepared from two or more plants.

12. A process for preparing dry plant extracts having a high content of plant ingredient wherein a fluid extract is fed into a vacuum drying system comprising a multi-blade stirrer extending through a cylindrical mixing and drying chamber and one of, or a combination of a vapor filter, a back-purge device, a solvent condenser comprising an after-cooler and a collecting vessel, a retrograde condenser and one of a process control and regulation unit or pelletizing dies, wherein the fluid extract to be dried is dried in a vacuum drying system consisting of a chopper extending throughout the entire depth of the drying and mixing chamber, the chopper having its own drive and knives rotating through a comb-shaped stator, the fluid extract is processed at a starting and return temperature between 120 and 5° C., an interior temperature between 10 and 80° C., a vapor temperature of 15 to 55° C. and a pressure between 0.5 and 1000 mbar, said drying being effected while the stirrer runs between 0 and 10 rpm, and the chopper operates at a rotational speed between 200 and 800 rpm.

13. A drug extract prepared by feeding a plant material to be dried into a vacuum drying system consisting of a chopper and a stirrer, and drying at a starting and return temperature between 120 and 5° C., an interior temperature between 10 and 80° C., a vapour temperature of 15° C to 55° C and a pressure between 0.5 and 1000 mbar, said drying being effected while the stirrer runs between 0 and 10 rpm, and the chopper operates at a rotational speed between 200 and 800 rpm.

14. An extract according to claim 13, which is an extract of *Herba thymi*.

15. An extract according to claim 13, which is an extract of *Agnus castus*.

16. An extract according to claim 13, which is an extract of Cimicifuga.

17. Pharmaceutical preparations with a high content of plant ingredients comprising a drug extract as well as additives and excipients, said drug extract prepared by feeding the plant material to be dried into a vacuum drying system consisting of a chopper and a stirrer, and drying at a starting and return temperature between 120 and 5° C., an interior temperature between 10 and 80° C. a vapor temperature of 15° C. to 55° C. and a pressure between 0.5 and 1000 mbar, said drying being effected while the stirrer runs between 0 and 10 rpm, and the chopper operates at a rotational speed between 200 and 800 rpm.

18. A preparation according to claim 17, which contains 0.5–8 mg, of Cimicifuga dry extract per 125 mg of the preparation.

19. A preparation according to claim 18 containing 1.66–2.86 mg Cimicifuga dry extract.

20. A preparation according to claim 17, which contains 1–10 mg, of *Agnus castus* dry extract per 125 mg of the preparation.

21. A preparation according to claim 20 containing 3.2 to 4.8 mg *Agnus castus* dry extract.

* * * * *